(12) United States Patent
Morelli et al.

(10) Patent No.: US 8,636,992 B2
(45) Date of Patent: Jan. 28, 2014

(54) THICKENER COMPOSITIONS COMPRISING SCLEROTIUM GUM AND A COPOLYMER

(75) Inventors: Muriel Morelli, Acquigny (FR); Agnes Le Fur, Anthony (FR); Carole Dupressoir, Poissy (FR)

(73) Assignee: Johnson & Johnson Consumer France SAS (FR)

( * ) Notice: Subject to any disclaimer, the term of this patent is extended or adjusted under 35 U.S.C. 154(b) by 2083 days.

(21) Appl. No.: 10/529,702

(22) PCT Filed: Sep. 30, 2003

(86) PCT No.: PCT/EP03/10921
§ 371 (c)(1),
(2), (4) Date: Jul. 11, 2006

(87) PCT Pub. No.: WO2004/028501
PCT Pub. Date: Apr. 8, 2004

(65) Prior Publication Data
US 2007/0166268 A1  Jul. 19, 2007

(30) Foreign Application Priority Data
Sep. 30, 2002  (EP) .................................... 02292407

(51) Int. Cl.
*A61K 8/73* (2006.01)
(52) U.S. Cl.
USPC ...................................................... 424/70.13

(58) Field of Classification Search
None
See application file for complete search history.

(56) References Cited

U.S. PATENT DOCUMENTS

| | | | |
|---|---|---|---|
| 5,425,939 A | 6/1995 | Guerrero et al. | |
| 5,441,740 A * | 8/1995 | Ozlen | 424/401 |
| 5,534,265 A | 7/1996 | Fowler et al. | |
| 5,554,647 A * | 9/1996 | Perricone | 514/474 |
| 5,643,586 A | 7/1997 | Perricone | |
| 5,807,561 A | 9/1998 | Guerrero | |
| 5,833,968 A | 11/1998 | Keil et al. | |
| 2003/0007985 A1 * | 1/2003 | Chevalier et al. | 424/401 |

FOREIGN PATENT DOCUMENTS

WO  WO 9844898 A1 * 10/1998

* cited by examiner

*Primary Examiner* — Nissa Westerberg

(57) ABSTRACT

This invention relates to chemical compositions comprising two thickening components, which are sclerotium gum and a copolymer selected from the group consisting of methyl vinyl ether/maleic anhydride copolymer and acryloyldimethyltaurate vinylpyrrolidone copolymer, in particular the ammonium salt of the latter; which components provide good thickening properties in the presence of electrolytes, in particular in the presence of ethanolamine or vitamin salts. Further there are provided cosmetic formulations comprising these thickening components.

5 Claims, No Drawings

THICKENER COMPOSITIONS COMPRISING SCLEROTIUM GUM AND A COPOLYMER

BRIEF DESCRIPTION OF THE INVENTION

This invention relates to chemical compositions comprising two thickening components, which provide good thickening properties in the presence of electrolytes, in particular in the presence of ethanolamine or vitamin salts. Further there are provided cosmetic formulations comprising these thickening components.

BACKGROUND OF THE INVENTION

Thickeners are often added to cosmetic formulations for a number of reasons such as to increase consistency, to improve their effectiveness and also for reasons of consumer perception. Formulations of increased viscosity are generally more convenient for application on the skin and moreover tend to remain on the areas of the skin to which they are applied, thus being more effective in delivering their skin beneficial effects. Moreover, formulations of thicker consistency have the additional benefit of conveying to the consumer a message of smoothness, softness, richness and luxuriousness.

A wide variety of thickeners have been developed because of the varying nature of the formulations in which they are applied. Indeed, not every thickener is equally effective in the wide spectrum of cosmetic formulations that require increased viscosity. The presence of certain components in such formulations may pose particular problems in that certain thickeners may prove out to be less effective. Formulations containing electrolytes pose a particular challenge in this regard in that these components tend to impair the effectiveness of thickeners, in particular of anionic thickeners. Another factor that influences effectiveness of the latter type of thickeners is pH. In particular at lower pH ranges (e.g. at pH lower than 7) anionic thickeners tend to lose their effectiveness.

A number of active ingredients in cosmetic formulations are electrolytes, examples being water-soluble vitamins but also certain amine compounds such as the ethanolamines. Such active ingredients find use in anti-aging formulations, which have become an important product category in skin care because of the shift of age distribution in the population and an increased attention to a youthful appearance.

It is known that, upon aging, skin becomes less elastic and develops fine lines and wrinkles, which are the direct result of deterioration of the supporting dermis layer. Further phenomena associated with skin aging are the appearance of pigment spots, skin thinning and skin sagging. Factors that play a role in skin aging are on the one hand intrinsic aging, which is part of the general aging process, and on the other extrinsic aging due to environmental factors. Amongst the latter there is photo-aging, which comprises damage caused to the skin due to the ultraviolet spectrum of sunlight. Anti-aging cosmetic products have been developed which contain vitamins or derivatives thereof, in particular vitamin A or its derivatives, such as alpha-hydroxy acids or retinoids, vitamin C, and certain plant extracts. These products, when applied on a regular basis during longer periods of time, have been shown to have a positive influence on the effects of skin aging.

The ethanolamine derivatives are a further class of components that have been developed for use in formulations to treat the effects of skin aging. U.S. Pat. No. 5,554,647 describes a method of treating aging skin and subcutaneous muscles comprising the use of an acetylcholine precursor such as dimethylaminoethanol (DMAE), also referred to as 'deanol', in an amount effective to produce increased muscle tone. U.S. Pat. No. 5,643,586 describes the topical treatment of subcutaneous muscle and overlying cutaneous tissue by applying a composition comprising a catecholamine precursor which in particular is tyrosine, phenylalanine or a mixture thereof preferably in combination with an acetylcholine precursor such as dimethylaminoethanol.

DMAE is currently used as an anti-aging agent in a variety of cosmetic formulations usually under the form of appropriate salt forms. Formulations containing this active ingredient are most effective when used in formulations that have a pH that is in the range of about pH 5.5 to about pH 7. At these pH values, the ethanolamine is present as a salt form and salts that are typically used are those derived from citric, malic and glycolic acid, including mixtures thereof. Usually, DMAE is formulated as a double salt, in particular a double salt of glycolic and citric acid. DMAE in this form occurs as an electrolyte.

Many of these formulations require increased viscosity, which poses a challenge in terms of stability of such formulations. As mentioned above, the presence of electrolytes in thickened cosmetic compositions destabilizes the activity of the thickening agents and typically results in an often strong decrease of the viscosity. Providing thickened formulations containing DMAE salts of acceptable stability therefore poses a particular challenge.

Thickeners and thickening systems have been described in the prior-art. European patent N° 0 684 039 and corresponding U.S. Pat. No. 5,425,939 describe a combination of sclerotium gum and hydrophobically modified acrylate or methacrylate having highly effective thickening properties. U.S. Pat. No. 5,833,968 discloses hair-fixing compositions in the form of a viscous gel containing homopolymers of acrylic acid, acrylic acid acrylamides copolymers and sclerotium gum. U.S. Pat. No. 5,807,561 discloses a composition for enhancing whitening effect on skin comprising a thickening polymer selected from sclerotium gum and xanthan gum and mixtures thereof. WO 01/70271 describes acid-stable compositions comprising sclerotium gum and carrageenan.

Although these references teach thickening systems with attractive properties, there is still a need for thickened formulations containing DMAE salts of acceptable stability. Additionally there is a more general need for thickening systems that provide adequate thickening properties in the presence of electrolytes. There is further need to provide thickened compositions containing an electrolyte wherein the viscosity remains stable. There is a more particular need to provide thickened formulations containing ethanolamine salts, in particular containing salts of DMAE, in particular such compositions having a pH, which is in the range of pH 4.5 to pH 8, in particular in the range of pH 5.5 to pH 7. There is another specific need to provide formulations containing ethanolamine or vitamin C salts and a thickener composition, which have a sufficiently long shelf life. Providing formulations that provide a solution to these needs or some of these needs is an object of the present invention.

SUMMARY OF THE INVENTION

The present invention is directed to a chemical composition comprising:
(a) sclerotium gum;
(b) a copolymer selected from the group consisting of methyl vinyl ether/maleic anhydride copolymer and acryloyldimethyltaurate vinylpyrrolidone copolymer, in particular the ammonium salt of the latter; and
(c) a suitable carrier.

Said chemical composition may be used to thicken compositions that contain an electrolyte.

In a further aspect there is provided a chemical composition comprising:
(a) sclerotium gum;
(b) a copolymer selected from the group consisting of methyl vinyl ether/maleic anhydride copolymer and acryloyldimethyltaurate vinylpyrrolidone copolymer, in particular the ammonium salt of the latter;
(c) one or more electrolytes; and
(d) a suitable carrier.

In a particular aspect this invention concerns a chemical composition comprising:
(a) from 0.005 to 3%, and in particular from 0.005 to 1% of sclerotium gum
(b) a from 0.005 to 3% and in particular from 0.005 to 1% of a copolymer selected from the group consisting of PVM/MA crosspolymer and ammonium acryloyl dimethyl taurate vinylpyrrolidone copolymer
(c) a suitable carrier.

In a further aspect there is provided a chemical composition comprising components (a), (b), and (c) as defined in the preceding paragraph and further:
(d) from 0.001% to 5%, in particular from 0.001% to 3%, further in particular from 0.005% to 1.5% of one or more electrolytes.

The invention further relates to a thickened composition, as defined above, having a pH in the range of about 4.5 to about 8, in particular of about 5.5 to about 7.

The invention further is concerned with a topical formulation comprising a composition as defined in this specification and claims and further ingredients. The topical formulation can be for dermatological use, but in particular is for cosmetic use. In an alternative aspect this invention provides the use of a chemical composition as defined in this specification and claims as a thickening system in a topical formulation for cosmetic or dematological use.

In a further aspect there is provided a dermatological or cosmetical formulation comprising a chemical composition as defined herein, and an effective amount of at least one ethanolamine derivative of formula I, or a topically acceptable salt thereof:

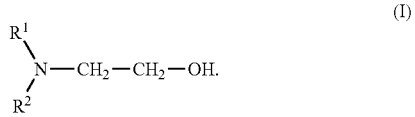

(I)

In another aspect the invention provides the use of a composition as defined herein for manufacturing a topical or in particular a cosmetic formulation.

DETAILED DESCRIPTION OF THE INVENTION

Unless indicated otherwise, all % are w/w relative to the total weight of the composition of formulation.

The compositions of the invention contain sclerotium gum. This material is a polymerized glucose, which can be obtained from a variety of fungi containing either glucose or fructose as described e.g. in U.S. Pat. No. 5,425,939. Sclerotium gum is used as a thickener and gelling agent. A particularly suitable sclerotium gum is the material available from Alban Mueller International under the trade name Amigel™ or Amigel Granule™.

One of the copolymers for use in the compositions of this invention is acryloyldimethyltaurate vinylpyrrolidone copolymer, in particular the ammonium salt of the latter. This is a copolymer obtained by copolymerisation of acylamidopropane sulfonic acid and vinylpyrrolidone in the presence of a suitable base and a cross-linking agent. The suitable base may be a basic amine derivative, i.e. any basic amine that does not interact with the copolymer or its monomeric building blocks, for example cyclic or non-cyclic alkylamines, benzylamines etc., but preferably is ammonia. Preferred are the materials known under Chemical Abstract registration Nos. 58374-69-9, 13162-05-5 and 88-12-0, available under the tradename Aristoflex AVC™ from the company Clariant.

Another type of copolymers for use in the compositions of this invention is methyl vinyl ether/maleic anhydride copolymer, also referred to as PVM/MA copolymer. Particular such copolymers are those, which are cross-linked with 1,9-decadiene, also referred to as PVM/MA Decadiene Crosspolymer. Preferred are the materials available under the Tradename Stabileze™ such as Stabilileze 06™ and Stabileze QM™ from the company ISP.

Both types of copolymers are known gelling agents and are used as thickeners.

The compositions of the invention additionally contain a carrier, which can be any of a variety of skin-compatible materials. Usually the carrier is of aqueous nature and the compositions of the invention are aqueous compositions.

This invention relates to chemical compositions as defined herein, which can be used as thickening systems in topical formulations, in particular in formulations containing one or more electrolytes. The formulations of the invention usually are aqueous in nature.

Thus in a further aspect this invention relates to topical formulations comprising a composition as defined herein. The topical formulations of the invention may be derived from the compositions of the invention, e.g. by adding further ingredients, or they may be derived directly from the components making up the compositions, e.g. by preparing the formulation without passing via a composition of the invention. Topical formulations comprise dermatological formulations (or topical pharmaceutical formulations), as well as cosmetic formulations.

The topical formulations of this invention may further contain any other ingredients or additives typically used in dermatological or in cosmetic formulations, including active ingredients. Examples of further ingredients or additives are surfactants, emulsifiers, consistency factors, conditioners, emollients, skin caring ingredients, moisturizers, humectants, thickeners, lubricants, chelating agents, fillers, binding agents, anti-oxidants, preservatives, active ingredients, in particular dermatologically active ingredients, fragrances, dyes, opacifying agents, and the like, provided that they are physically and chemically compatible with the other components of the composition. Active ingredients as mentioned herein comprise, for example, anti-inflammatory agents, anti-bacterials, anti-fungals, anti-irritating compounds, anti-itching agents, moisturising agents, skin caring ingredients, plant extracts, vitamins, and the like. Also included are sunscreen actives which may be inorganic or organic in nature. Of particular interest are any active ingredients suited for topical applications.

The topical formulations of the invention are any such formulations having increased viscosity, in particular creams, ointments and gels, but also, any aqueous based formulations where higher viscosity is a desirable attribute. Such formulations may take the form of foundations, sunscreen formulations, moisturizers, hairstyling gels, shampoos, nail varnish removers, emulsions, lotions, foaming products, etc. The emulsion-based formulations may be, for example, in the form of oil-in-water, or multiple emulsions (W/O/W). Of particular interest are formulations based on oil-in-water emulsions.

Examples of suitable preservatives for use in the compositions or formulations of the invention include the $C_1$-$C_4$ alkyl parabens and phenoxyethanol. Generally, the preservative is present in an amount ranging from about 0.5 to about 2.0, preferably about 1.0 to about 1.5, weight percent based on the total composition. In a preferred embodiment, the preservative is mixture of from about 0.2 to about 0.5 weight percent methylparaben, from about 0.2 to about 5.0 weight percent propylparaben and from about 0.05 to about 0.10 weight percent butylparaben.

Preferably, antioxidants should be present in the compositions or formulations according to the invention. Suitable antioxidants include butylated hydroxy toluene (BHT), ascorbyl palmitate, butylated hydroanisole (BHA), phenyl-α-naphthylamine, hydroquinone, propyl gallate, nordihydroquiaretic acid, vitamin E or derivatives of vitamin E, vitamin C and derivatives thereof, calcium pantothenic, green tea extracts and mixed polyphenols, and mixtures thereof. When utilized, the antioxidant can be present in an amount ranging from about 0.02 to about 0.5% by weight, more preferably from about 0.002 to about 0.1% by weight of the total composition.

Emollients which can be included in the compositions or formulations of the invention function by their ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of suitable emollients include, but are not limited to, polypropylene glycol ("PPG")-15 stearyl ether, PPG-10 cetyl ether, steareth-10, oleth-8, PPG4 lauryl ether, vitamin E acetate, PEG-7 glyceryl cocoate, lanolin, cetyl alcohol, octyl hydroxystearate, dimethicone, and combinations thereof. Cetyl alcohol, octyl hydroxystearate, dimethicone, and combinations thereof are preferred. When utilized, the emollient can be present in an amount from about 0.01 to about 5, preferably from about 1 to about 4 percent by weight based on the total composition.

Polyhydric alcohols can be utilized as humectants in the compositions or formulations of the invention. The humectants aid in increasing the effectiveness of the emollient, reduce scaling, stimulate removal of built-up scale and improve skin feel. Suitable polyhydric alcohols include, but are not limited to, glycerol (also known as glycerin), polyalkylene glycols, alkylene polyols and their derivatives, including butylene glycol, propylene glycol, dipropylene glycol, polypropylene glycol, polyethylene glycol and derivatives thereof, sorbitol, hydroxypropyl sorbitol, hexylene glycol, 1,3-dibutylene glycol, 1,2,6,-hexanetriol, ethoxylated glycerol, propoxylated glycerol and mixtures thereof. Glycerin is preferred. When utilized, the humectant is present in an amount from about 0.1 to about 5, preferably from about 1 to about 3 percent by weight, based on the total weight of the composition.

In particular embodiments, the compositions or formulations of this invention contain one or more electrolytes. These electrolytes can be salts, either inorganic or organic. Organic salts may be salts of organic acids with inorganic cations or of organic bases with inorganic anions. Particular embodiments of this invention are those wherein the electrolytes are salts of active ingredients. In specific embodiments these salts are ethanolamine salts or vitamin salts, e.g. DMAE salts or salts of Vitamin C.

In a particular aspect, this invention relates to compositions or topical formulations as specified herein with relatively high concentrations of electrolytes. For example, these formulations may contain more than 0.5%, or more than 1%, in particular more than 2%, more in particular more than 3% of electrolyte.

Of particular interest are compositions or formulations as specified herein which additionally contain an ethanolamine derivative of formula I, or a topically acceptable acceptable salt thereof:

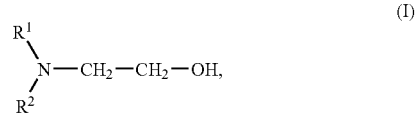

In formula (I) $R^1$ and $R^2$ independently represent hydrogen, $C_{3-6}$ cycloalkyl or $C_{1-6}$ alkyl, optionally substituted with hydroxy, methoxy, oxo or formyl.

Preferably $R^1$ and $R^2$ independently represent $C_{1-4}$ alkyl.

The most preferred ethanolamine of formula I is dimethylaminoethanol (MA), also referred to as deanol.

In a further particular aspect there are provided compositions or topical formulations as specified herein that additionally contain DMAE salts or salts of water-soluble vitamins. The invention additionally concerns the use of a composition as specified in this specification and claims, as a thickening system that can be used for preparing thickened topical formulations and in particular thickened DMAE salt containing formulations. The thickening system can also be used as a thickening system in formulations containing other ionic agents such as water-soluble vitamin salts. Particular water soluble vitamin salts are vitamin C salts more in particular those salts derived from alkali metal or alkaline earth metal bases, or from suitable organic bases. The latter may be any organic base that does not interact with the vitamin C molecule.

Certain embodiments of this invention that are of particular interest therefore are chemical compositions or formulations comprising:

(a) sclerotium gum;
(b) a copolymer selected from the group consisting of methyl vinyl ether/maleic anhydride copolymer and acryloyldimethyltaurate vinylpyrrolidone copolymer, in particular the ammonium salt of the latter;
(c) one or more electrolytes; and
(d) a suitable carrier.

Of further particular interest are those compositions or formulations as defined above wherein the electrolyte or electrolytes are selected from the group of compounds of formula (I) as defined and specified herein above.

The compositions of this invention can be made by following art-known procedures, e.g. by mixing the ingredients together with or in a suitable carrier material.

The components in the compositions and formulations according to the present invention act synergistically, i.e. there is synergism in the properties of sclerotium gum and each or both of the copolymers. More in particular there is synergy in the thickening and gelling properties of these components, especially in the presence of electrolytes. Moreover, the compositions of this invention provide stable thickening systems, i.e. their thickening activity is not changed over longer periods of time or only changes marginally, or alternatively, formulations thickened with these compositions will have the same degree of viscosity during a relatively long period of time, or the viscosity will only change marginally. With stable thickening activity it is meant that formulations thickened with the compositions of the invention can be stored at standard conditions during periods of time, which are common in the trade, in particular in the trade of cosmetics. In particular the integrity, as far as its viscosity is concerned, will remain chemically unaffected. The compositions of the invention and the topical formulations derived thereof remain intact during standard shelf-life periods at ambient temperature, e.g. longer than 2 years at a temperature of about 25° C.

This makes the compositions particularly useful as thickening systems in formulations that contain electrolytes, in particular in such formulations containing relatively high amounts of electrolytes, more specifically, in formulations containing DMAE and its salts and/or vitamins and their salts (specifically ascorbic acid salts). The compositions can be used as a thickening system which is particularly effective with high concentrations of DMAE salts (e.g. compositions or formulations containing up to 3% DMAE salts, said salts being obtained by adding one or more appropriate acids, in particular glycolic and citric acid) or of vitamin C (e.g. compositions or formulations containing up to 3% of vitamin C salts).

The w/w ratio of sclerotium gum to the total amount of the vinyl ether/maleic anhydride and/or acryloyldimethyltaurate vinylpyrrolidone copolymers in the compositions and formulations of the invention may be in the range of from 40:1 to 1:40, or in the range of from 20:1 to 1:20, or in particular of from 10:1 to 1:10, or more in particular in the range from 5:1 to 1:5, preferably in the range of from 10:1 to 1:2, more preferably in the range of from 5:1 to 1:1 or from 3:1 to 1:1 or from 2:1 to 1:1.

Formulations for end use may contain sclerotium gum at concentrations, which are in the range from 0.05% to 3%, in particular from 0.1% to 2%, more in particular from 0.2% to 1.5%. Said formulations may contain copolymer at concentrations, which are in the range from 0.05% to 3%, in particular from 0.1% to 2%, more in particular from 0.2% to 1.5%. The chemical compositions of the invention may contain these components at the same concentrations or at higher concentrations, e.g. where these compositions are used as concentrates.

The formulations according to the present invention can be prepared by adding the appropriate ingredients to a composition of the invention, or vice versa by adding the composition to an appropriate cosmetic or dermatological formulation base. It is also possible to mix all the ingredients individually, i.e. without making a separate composition as defined herein.

Particular embodiments of the present invention are topical formulations comprising:
  (a) sclerotium gum;
  (b) methyl vinyl ether/maleic anhydride copolymer and
  (c) a suitable carrier.

Other particular embodiments of the present invention are topical formulations comprising:
  (a) sclerotium gum;
  (b) acryloyldimethyltaurate vinylpyrrolidone copolymer, in particular the ammonium salt of the latter; and
  (c) a suitable carrier.

Further particular embodiments are topical formulations comprising
  (a) sclerotium gum;
  (b) methyl vinyl ether/maleic anhydride copolymer;
  (c) one or more electrolytes; and
  (d) a suitable carrier.

Other particular embodiments are topical formulations comprising
  (a) sclerotium gum;
  (b) acryloyldimethyltaurate vinylpyrrolidone copolymer, in particular the ammonium salt of the latter;
  (c) one or more electrolytes; and
  (d) a suitable carrier.

Other embodiments are topical formulations comprising:
  (a) 0.05% to 3% in particular from 0.1% to 2%, more in particular from 0.2% to 1.5% of sclerotium gum;
  (b) 0.05% to 3% in particular from 0.1% to 2%, more in particular from 0.2% to 1.5% of methyl vinyl ether/maleic anhydride copolymer and
  (c) a suitable carrier.

Other particular embodiments of the present invention are topical formulations comprising:
  (a) 0.05% to 3% in particular from 0.1% to 2%, more in particular from 0.2% to 1.5% of sclerotium gum;
  (b) 0.05% to 3% in particular from 0.1% to 2%, more in particular from 0.2% to 1.5% of acryloyldimethyltaurate vinylpyrrolidone copolymer, in particular the ammonium salt of the latter; and
  (c) a suitable carrier.

Further particular embodiments are topical formulations comprising
  (a) 0.05% to 3% in particular from 0.1% to 2%, more in particular from 0.2% to 1.5% of sclerotium gum;
  (b) 0.05% to 3% in particular from 0.1% to 2%, more in particular from 0.2% to 1.5% of methyl vinyl ether/maleic anhydride copolymer;
  (c) at least 0.5% of one or more electrolytes; and
  (d) a suitable carrier.

Other particular embodiments are topical formulations comprising
  (a) 0.05% to 3% in particular from 0.1% to 2%, more in particular from 0.2% to 1.5% of sclerotium gum;
  (b) 0.05% to 3% in particular from 0.1% to 2%, more in particular from 0.2% to 1.5% of acryloyldimethyltaurate vinylpyrrolidone copolymer, in particular the ammonium salt of the latter;
  (c) at least 0.5% of one or more electrolytes; and
  (d) a suitable carrier.

Particular embodiments of the present invention are topical formulations comprising:
  (a) sclerotium gum;
  (b) methyl vinyl ether/maleic anhydride copolymer and
  (c) a suitable carrier
wherein the w/w ratio of of sclerotium gum to the total amount of the vinyl ether/maleic anhydride and/or copolymer in the formulations of the invention is in the range of from 40:1 to 1:40, or in the range of from 20:1 to 1:20, or in particular of from 10:1 to 1:10, or more in particular in the range from 5:1 to 1:5, preferably in the range of from 10:1 to 1:2, more preferably in the range of from 5:1 to 1:1 or from 3:1 to 1:1 or from 2:1 to 1:1.

Other particular embodiments of the present invention are topical formulations comprising:
  (a) sclerotium gum;
  (b) acryloyldimethyltaurate vinylpyrrolidone copolymer, in particular the ammonium salt of the latter; and
  (c) a suitable carrier
wherein the w/w ratio of sclerotium gum to the total amount of acryloyldimethyltaurate vinylpyrrolidone copolymer in the formulations is in the range of from 40:1 to 1:40, or in the range of from 20:1 to 1:20, or in particular of from 10:1 to 1:10, or more in particular in the range from 5:1 to 1:5, preferably in the range of from 10:1 to 1:2, more preferably in the range of from 5:1 to 1:1 or from 3:1 to 1:1 or from 2:1 to 1:1.

Further particular embodiments are topical formulations comprising
(a) sclerotium gum;
(b) methyl vinyl ether/maleic anhydride copolymer;
(c) one or more electrolytes; and
(d) a suitable carrier wherein the w/w ratio of sclerotium gum to the total amount of the vinyl ether/maleic anhydride copolymer in the formulations is in the range of from 40:1 to 1:40, or in the range of from 20:1 to 1:20, or in particular of from 10:1 to 1:10, or more in particular in the range from 5:1 to 1:5, preferably in the range of from 10:1 to 1:2, more preferably in the range of from 5:1 to 1:1 or from 3:1 to 1:1 or from 2:1 to 1:1.

Other particular embodiments are topical formulations comprising
(a) sclerotium gum;
(b) acryloyldimethyltaurate vinylpyrrolidone copolymer, in particular the ammonium salt of the latter;
(c) one or more electrolytes; and
(d) a suitable carrier wherein the w/w ratio of sclerotium gum to the total amount of acryloyldimethyltaurate vinylpyrrolidone copolymers in the formulations is in the range of from 40:1 to 1:40, or in the range of from 20:1 to 1:20, or in particular of from 10:1 to 1:10, or more in particular in the range from 5:1 to 1:5, preferably in the range of from 10:1 to 1:2, more preferably in the range of from 5:1 to 1:1 or from 3:1 to 1:1 or from 2:1 to 1:1.

Without being bound to theory it is believed that the thickening system in the compositions and formulations of this invention function as follows. Used alone, the thickeners form structural networks in the liquid that are sensitive to electrolytes (the structural networks are deteriorated by electrolytes and viscosity drops). It is believed that in the compositions and formulations of the invention both thickeners form a special type of structural network that better resist deterioration by electrolytes, probably due to a particular tridimensional structural organization of the networks.

The following examples are meant to illustrate the present invention, not to limit it thereto.

EXAMPLES

In the following examples, the ingredients are mixed in the sequence they are listed in a standard vessel equipped with a mixer.

Example 1

| | |
|---|---|
| Aqua | 94.26% |
| Sclerotium Gum | 0.80% |
| Glycerin | 3.00% |
| Phenoxyethanol | 0.30% |
| Methylparaben | 0.10% |
| Propylparaben | 0.04% |
| Ammonium Acryloyldimethyltaurate/VP Copolymer | 1.50% |
| Total | 100% |

Example 2

| | |
|---|---|
| Aqua | 94.76% |
| Sclerotium Gum | 0.80% |
| Glycerin | 3.00% |
| Phenoxyethanol | 0.30% |
| Methylparaben | 0.10% |
| Propylparaben | 0.04% |
| Ammonium Acryloyldimethyltaurate/VP Copolymer | 1.00% |
| Total | 100% |

Example 3

| | |
|---|---|
| Aqua | 78.290% |
| Disodium EDTA | 0.080% |
| Sclerotium Gum | 0.800% |
| Glycerin | 3.000% |
| Glyceryl Polymethacrylate | 2.010% |
| Propylene Glycol | 0.030% |
| Aqua | 0.960% |
| Tyrosine | 1.500% |
| Hydrogenated polyisobutene | 1.500% |
| Butylene Glycol | 3.000% |
| Phenoxyethanol | 0.300% |
| Methylparaben | 0.100% |
| Propylparaben | 0.040% |
| Biosaccharide Gum-1 | 0.020% |
| Phenoxyethanol | 0.024% |
| Aqua | 1.956% |
| Sodium Hydroxide | 0.100% |
| DMAE | 1.000% |
| Citric Acid | 0.320% |
| Glycolic Acid | 0.320% |
| Cyclopentasiloxane | 3.000% |
| Ammonium Acryloyldimethyltaurate/VP Copolymer | 1.500% |
| Perfume | 0.150% |

Example 4

| | |
|---|---|
| Aqua | 78.110% |
| Disodium EDTA | 0.080% |
| Sclerotium Gum | 0.800% |
| Glycerin | 3.000% |
| Glyceryl Polymethacrylate | 2.010% |
| Propylene Glycol | 0.030% |
| Aqua | 0.960% |
| Tyrosine | 0.500% |
| Butylene Glycol | 3.000% |
| Phenoxyethanol | 0.300% |
| Methylparaben | 0.100% |
| Propylparaben | 0.040% |
| Biosaccharide Gum-1 | 0.020% |
| Phenoxyethanol | 0.024% |
| Aqua | 1.956% |
| Sodium Hydroxide | 0.100% |
| DMAE | 2.500% |
| Citric Acid | 1.200% |
| Glycolic Acid | 1.120% |
| Cyclopentasiloxane | 3.000% |
| Ammonium Acryloyldimethyltaurate/VP Copolymer | 1.000% |
| Perfume | 0.150% |

Example 5

| | |
|---|---|
| Aqua | 84.90% |
| Sclerotium gum | 0.75% |
| Arachidyl alcohol | 1.00% |
| Behenyl Alcohol | |
| Arachidyl glucoside | |
| Caprylyl glycol | 0.50% |
| Glycerin | 2.00% |
| Methylparaben | 0.15% |
| Sodium Methyl Paraben | 0.35% |
| Sodium Propyl Paraben | |
| Sodium Ethyl Paraben | |
| Dimethicone | 2.00% |
| Cyclopentansiloxane | 2.00% |
| Ammonium Acryloyldimethyltaurate/VP Copolymer | 1.00% |
| Citric acid | 2.60% |
| DMAE | 2.50% |
| Perfume | 0.25% |
| Total | 100.00% |

Example 6

| | |
|---|---|
| Aqua | 73.13% |
| Sclerotium Gum | 0.80% |
| Ammonium Acryloyl Dimethyltaurate/VP copolymer | 1.00% |
| Disodium EDTA | 0.10% |
| Glycerine | 5.00% |
| Methylparaben | 0.30% |
| PEG-100 Stearate | 2.00% |
| Glyceryl Stearate | |
| Stearyl Alcohol | 1.50% |
| Isodecyl Neopentanoate | 4.00% |
| Phenoxyethanol | 0.60% |
| Isononyl Isononanoate | 4.00% |
| Propylparaben | 0.15% |
| BHT | 0.07% |
| Tocopheryl Acetate | 0.10% |
| Cyclopentasiloxane | 1.00% |
| PEG-8 | 1.00% |
| Butylene Glycol | 2.00% |
| Neoruscogenine/Ruscogenine | 0.05% |
| Ascorbic Acid | 0.05% |
| Citric acid | 0.40% |

-continued

| | |
|---|---|
| Glycolic Acid | 0.70% |
| Aqua | |
| DMAE | 1.00% |
| Aluminum Starch Octenyl Succinate | 1.00% |
| Perfume | 0.05% |
| Total | 100% |

The invention claimed is:

1. A chemical composition comprising:
 (a) from 0.005 to 3 wt. % of sclerotium gum;
 (b) from 0.005 to 3 wt. % of a copolymer selected from the group consisting of methyl vinyl ether/maleic anhydride copolymer and acryloyldimethyltaurate vinylpyrrolidone copolymer
 (c) an aqueous carrier; and
 (d) at least 0.5 wt. % of at least one ethanolamine derivative of formula I, or a topically acceptable salt thereof:

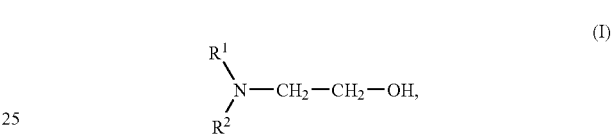

(I)

wherein in formula I, $R^1$ and $R^2$ independently represent hydrogen, $C_{3-6}$ cycloalkyl or $C_{1-6}$ alkyl, optionally substituted with hydroxy, ethoxy, oxo or formyl, wherein the pH of the composition ranges from about 4.5 to about 8.

2. A chemical composition according to claim 1, wherein said copolymer is an ammonium salt of acryloyldimethyltaurate vinylpyrrolidone copolymer.

3. A chemical composition according to claim 1 comprising:
from 0.005 to 1 wt. % of said sclerotium gum and
from 0.005 to 1 wt. % of said copolymer.

4. A formulation according to claim 1 wherein the ethanolamine of formula I is a mixed glycolate/citrate salt of dimethylethanolamine.

5. A formulation according to claim 1, wherein the electrolyte is a Vitamin C salt.

* * * * *